(12) United States Patent
Slade et al.

(10) Patent No.: US 9,782,154 B2
(45) Date of Patent: Oct. 10, 2017

(54) INSTRUMENT FOR MANIPULATING AN IMPLANT

(75) Inventors: Jonathan James Slade, Pontypridd (GB); Marc David Elliott, Llantrisant (GB)

(73) Assignee: Biomet UK Healthcare Limited (GB)

(*) Notice: Subject to any disclaimer, the term of this patent is extended or adjusted under 35 U.S.C. 154(b) by 842 days.

(21) Appl. No.: 13/991,040

(22) PCT Filed: Dec. 1, 2011

(86) PCT No.: PCT/GB2011/052376
§ 371 (c)(1),
(2), (4) Date: Sep. 18, 2013

(87) PCT Pub. No.: WO2012/073033
PCT Pub. Date: Jun. 7, 2012

(65) Prior Publication Data
US 2014/0005641 A1    Jan. 2, 2014

(30) Foreign Application Priority Data
Dec. 2, 2010 (GB) .................................. 1020425.3

(51) Int. Cl.
*A61B 17/00* (2006.01)
*A61F 2/46* (2006.01)
*A61F 2/34* (2006.01)

(52) U.S. Cl.
CPC ............ *A61B 17/00* (2013.01); *A61F 2/4609* (2013.01); *A61F 2/4637* (2013.01); *A61F 2/34* (2013.01); *A61F 2002/4685* (2013.01)

(58) Field of Classification Search
CPC .................. A61F 2/4609; A61F 2/4637; A61F 2002/4685; A61B 2017/00407
See application file for complete search history.

(56) References Cited

U.S. PATENT DOCUMENTS 4,846,429 A * 7/1989 Scheurer ................ F16B 47/00
                                                        248/205.8
6,626,913 B1    9/2003 McKinnon et al.
(Continued)

FOREIGN PATENT DOCUMENTS

JP        55135815         3/1979
JP        55135815 A      10/1980
(Continued)

OTHER PUBLICATIONS

"International Application Serial No. PCT/GB2011/052376, International Preliminary Report on Patentability dated Jun. 13, 2013", 9 pgs.

(Continued)

*Primary Examiner* — Lynsey Eiseman
*Assistant Examiner* — Amanda Steinberg
(74) *Attorney, Agent, or Firm* — Schwegman Lundberg & Woessner, P.A.

(57) ABSTRACT

An instrument (2) for manipulating an implant is disclosed, the instrument (2) comprising an attachment element (22), which is operable to engage an implant, an actuation rod (20), a distal end (34) of which is connected to the attachment element (22) and a handle (4) having a gripping surface (6). At least a proximal end (32) of the actuation rod (20) is moveably received within the handle (4). The instrument further comprises a drive mechanism (42), mounted on the handle (4) and operable to drive relative movement between the actuation rod (20) and the handle (4). Also disclosed is an instrument (2) for manipulating an implant, the instrument (2) comprising a handle (4), a suction cup (22) operable to engage a surface of an implant and moveably mounted with respect to the handle (4), and a release cord (104), fixedly connected between an edge (88) of the suction cup (22) and the handle (4). A method of releasing an (Continued)

implant from an instrument (2) to which it is attached is also disclosed. The method comprises displacing the suction cup (22) and associated implant with respect to the handle (4) until the release cord (104) causes peel back of the edge (88) of the suction cup (22).

17 Claims, 13 Drawing Sheets

(56) References Cited

U.S. PATENT DOCUMENTS

| | | | | |
|---|---|---|---|---|
| 2005/0137603 | A1* | 6/2005 | Belew | A61F 2/4609 606/91 |
| 2007/0093850 | A1* | 4/2007 | Harris | A61F 2/4611 606/99 |
| 2008/0287957 | A1 | 11/2008 | Hester et al. | |
| 2009/0216240 | A1* | 8/2009 | Posdal | A61F 2/4609 606/99 |
| 2010/0121386 | A1* | 5/2010 | Peultier | A61B 17/7086 606/86 A |
| 2011/0288649 | A1* | 11/2011 | Ratzel | A61F 2/4637 623/22.24 |
| 2012/0029524 | A1* | 2/2012 | Imhof-Rothlin | A61F 2/4609 606/99 |

FOREIGN PATENT DOCUMENTS

| | | |
|---|---|---|
| JP | 07039677 | 7/1995 |
| JP | 07039677 U | 7/1995 |
| JP | 2006315101 A | 11/2006 |
| JP | 5074676 B2 | 11/2012 |
| WO | WO-2010/052500 A2 | 5/2010 |
| WO | WO-2012073033 A1 | 6/2012 |

OTHER PUBLICATIONS

"International Application Serial No. PCT/GB2011/052376, Written Opinion dated Feb. 21, 2012", 7 pgs.

"Japanese Application No. 2013-541428, Office Action dated Sep. 16, 2015", (W/ English Translation), 14 pgs.

International Search Report for PCT/GB2011/052376, dated Feb. 21, 2012; ISA/EP.

"Australian Application Serial No. 2011334640, Examination Report dated Jun. 1, 2015", 3 pgs.

"Japanese Application Serial No. 2013-541428, Examiners Decision of Final Refusal dated Apr. 11, 2016", 7 pgs.

"Japanese Application Serial No. 2013-541428, Reason for Rejection dated Sep. 16, 2015", 5 pgs.

"Japanese Application Serial No. 2013-541428, Response filed Mar. 16, 2016 to Reason for Rejection dated Sep. 16, 2015", with English translation of claims, 19 pgs.

"Australian Application Serial No. 2011334640, Response filed Oct. 1, 2015 to Examination Report dated Jun. 1, 2015", 16 pgs.

"Australian Application Serial No. 2011334640, Response filed Oct. 1, 2015 to Examination Report dated Jun. 1, 2015", 16 pgs, \* cited by examiner

INSTRUMENT FOR MANIPULATING AN IMPLANT

CROSS-REFERENCE TO RELATED APPLICATIONS

This application is a 371 U. S. National Stage of International Application No. PCT/GB2011/052376, filed on Dec. 1, 2011 and published in English as WO 2012/073033 A1 on Jun. 7, 2012. This application claims priority to British Patent Application No. 1020425.3, filed on Dec. 2, 2010. The disclosures of the above applications are incorporated herein by reference in their entirety.

The present invention relates to an instrument for manipulating an implant, and particularly, but not exclusively, relates to an instrument for handling and impaction of a joint prosthesis component, such as an acetabular cup.

BACKGROUND

During a joint replacement procedure, it is necessary to manipulate prosthesis components into their required positions with respect to patient anatomy. In the case for example of a hip replacement prosthesis, it is necessary to manoeuvre an acetabular cup into a prepared patient acetabulum, and it may also be necessary to impact the cup into the prepared recess. It is known to use specific tools for the manipulation and impaction of prosthesis components in this manner.

In order to allow a gripping or impaction tool to gain purchase on an implant, it is usual for the implant to include one or more attachment features onto which the gripping and/or impaction tool can engage in order to manipulate the implant. This is particularly the case with acetabular cups, which do not otherwise lend themselves to easy engagement with a gripping or impaction tool. Typical attachment features for an acetabular cup might include a threaded apical bore, operable to receive a threaded rod, as well as projecting lugs and undercuts, all designed to engage with corresponding attachment features on a gripping and/or impaction instrument. This arrangement works well for multiple body acetabular cups, of kind to comprise an external shell and separate internal bearing component. In this type of construction, the external shell may be provided with any appropriate attachment features for interaction with a gripping or impaction tool. Once in place, these attachment features are completely covered by the separate bearing component that is fitted into the outer shell.

Attachment to a gripping or impaction tool becomes more problematic when considering single body, or so called monobloc acetabular cups. This type of implant component comprises a single body having an outer bone engaging surface and an inner bearing surface. In such a component, the capacity to accommodate additional attachment features is severely limited. The internal bearing surface must remain free of any surface discontinuities or other aberrations and thus is not available for the provision of attachment features. Even temporary attachment mechanisms have proven extremely difficult to implement. The condition of the bearing surface is vital to the success and longevity of the implant. Thus, any temporary attachment procedure must be carefully controlled to ensure that no possibility of damage to the highly polished bearing surface can arise. Similar issues are also encountered in the assembly of a multiple body acetabular cup. As noted above, the shell component of a modular acetabular prosthesis may comprise attachment features, as these will be covered once the prosthesis is assembled. However, the bearing component must also be gripped and manipulated into place on the shell, and, as in the case of a monoblock cup, the internal bearing surface of the bearing component must remain smooth and the risk of damage to the surface must be minimised.

An additional issue that must be considered within the context of implant manipulation is the release of the implant from the relevant tool once the implant is in position. The implant may be considerably less accessible once in position, and removal or release form a tool may involve gaining direct access to the implant through the wound incision. Such direct contact is undesirable and carries risks of additional accidental contact with the implant and consequent damage to the bearing surface.

SUMMARY OF THE INVENTION

According to the present invention, there is provided an instrument for manipulating an implant, the instrument comprising an attachment element, operable to engage an implant, an actuation rod, a distal end of which is connected to the attachment element, and a handle having a gripping surface, wherein at least a proximal end of the actuation rod is moveably received within the handle, the instrument further comprising a drive mechanism, mounted on the handle and operable to drive relative movement between the actuation rod and the handle.

The handle may be made from a metallic material such as stainless steel.

The drive mechanism may be mounted in the vicinity of the gripping surface and may for example be mounted immediately adjacent the gripping surface. Alternatively, the drive mechanism may be mounted substantially within the gripping surface.

According to one embodiment, the proximal end of the actuation rod may be slidably received within the handle. Substantially the entire length of the actuation rod may be received within the handle.

The drive mechanism may comprise an annular wheel, through which the proximal end of the actuation rod is received, the wheel may comprise an internal thread, which may be operable to engage a corresponding external thread formed on the proximal end of the actuation rod.

The threads on the wheel and actuation rod may comprise standard, buttress or truncated threads. The pitch of the threads may be varied according to functional requirements of the instrument.

The actuation rod and the handle may comprise cooperating formations operable to prevent relative rotation between the actuation rod and the handle. These formations may take the form of a keyway formed in the handle and a corresponding spigot formed on the actuation rod. The keyway and cooperating spigot may be located at the proximal end of the instrument.

The annular wheel may comprise a resilient ratchet arm on which the internal thread may be formed. The remaining internal surface of the annular wheel may be substantially free of surface features.

The remaining internal surface of the annular wheel may be substantially smooth, lacking any feature operable to engage the thread formed on the proximal end of the actuation rod.

The resilient ratchet arm may be sprung or otherwise biased to a preferred position.

The annular wheel may be received within a recess formed on the handle. The recess may take the form of a housing formed in the handle.

Adjacent annular surfaces of the wheel and handle may comprise cooperating formations operable to engage to limit relative rotation between the wheel and the handle.

Such cooperating formations may be selectively engageable, requiring for example relative axial force to be applied between the annular wheel and the handle. The cooperating formations may comprise a pair of lugs formed on an annular surface of the wheel and a corresponding recess which may be formed on an adjacent annular surface of the handle. The recess may be linear, curved or curvilinear.

The instrument may further comprise an impaction plate which may be removably mounted at a distal end of the handle.

The impaction plate may be mounted in fixed relation to the handle, and may for example comprise anti rotation features. The impaction plate may be formed from a polymer material or may be formed from a metallic or other suitable material.

The impaction plate may comprise an annular impaction surface, which may be operable to engage an annular surface of the implant.

The attachment element may comprise a suction cup.

The suction cup may be formed from a medical grade plastics material such as medical grade silicone. The suction cup may comprise an attachment lug which may be received within an attachment recess formed on the distal end of the actuation rod. The cooperating lug and recess may incorporate anti rotation features. The lug may be formed at a substantially central region of the suction cup, and may extend from a convex surface of the cup. The lug may be joined to the cup via a neck.

The suction cup may comprise a release mechanism.

The release mechanism may be operable to release a vacuum or partial vacuum formed between the suction cup and a surface of an implant.

The release mechanism may comprise a release tab, which may be operable to be held in fixed relation to the handle and may be connected to an edge of the suction cup via a release cord.

The release tab may be operable to engage on a corresponding release surface formed in the impaction plate. The release cord may be received within a slot or recess formed in the impaction plate.

The release tab may for example comprise a T bar, which may be retained via a release surface formed in the impaction plate.

The release cord may be integrally formed with the suction cup. The T bar may be integrally formed with the release cord. Alternatively, the release cord and suction cup may be separately formed from different materials. For example, the release cord may engage a lug formed on a rim of the suction cup.

The attachment element may comprise an external thread which may be formed on the distal end of the actuation rod.

The external thread may be sized to engage with an internal thread on an attachment bore formed within an implant to be manipulated.

The instrument may further comprise an alignment guide which may comprise a separate component releasably engageable on the handle of the instrument. The alignment guide may include openings or other features for receiving further guiding materials and may facilitate correct alignment of the instrument.

The instrument may for example be an instrument for gripping and impaction of an implant and may be suitable for gripping and impaction of an acetabular cup implant. The instrument may be suitable for gripping and impaction of a monoblock acetabular cup prosthesis, and/or may be suitable for gripping and manipulation of a bearing component of a modular acetabular cup prosthesis.

According to another aspect of the present invention, there is provided an instrument for manipulating an implant, the instrument comprising a handle, a suction cup operable to engage a surface of an implant and moveably mounted with respect to the handle, and a release cord, fixedly connected between an edge of the suction cup and the handle.

The suction cup may be connected to an end of an actuation rod which may be moveably mounted within the handle.

The actuation rod may be slidably mounted within the handle.

The release cord may be integrally formed with the suction cup and may terminate in a release tab. Alternatively, the release cord and suction cup may be separately formed from different materials. For example, the release cord may engage a lug formed on a rim of the suction cup.

The instrument may further comprise an impaction plate which may be mounted in fixed relation to the handle.

The release tab may be operable to engage a release surface formed on the impaction plate.

According to another aspect of the present invention, there is provided a method of releasing an implant from an instrument to which it is attached, the instrument comprising a handle, a suction cup operable to engage a surface of the implant and moveably mounted with respect to the handle, and a release cord, fixedly connected between an edge of the suction cup and the handle, the method comprising displacing the suction cup and associated implant with respect to the handle until the release cord causes peel back of the edge of the suction cup.

Displacement of the suction cup may be accomplished via an actuation rod. Displacement of the suction cup may be accomplished using a drive mechanism and may be driven from a location remote from the suction cup.

According to another aspect of the present invention, there is provided a method of manipulating an implant using an instrument as disclosed in the present specification, comprising the steps of:

(a) applying pressure to the ratchet arm of the annular wheel such that the internal threads of the ratchet arm maintain engagement with the external threads on the proximal end of the actuation rod, (b) preventing relative rotation between the wheel and the handle by holding the wheel in place, (c) applying the suction cup to an implant surface and applying pressure to engage at least a partial vacuum between the suction cup and the implant surface, (d) rotating the annular wheel to cause retraction of the actuating rod into the handle until the annular impaction surface of the impaction plate engages onto an annular surface of the implant, (e) rotating the annular wheel further to cause withdrawal of a central region of the suction cup from the implant surface, thus increasing the partial vacuum between the suction cup and implant surface, (f) manipulating the implant into a desired location using the instrument, (g) rotating the annular wheel to cause projection of the actuation rod out of the handle until the release tab and cord of the suction cup are engaged, (h) rotating the annular wheel further to cause peel back of the suction cup from the implant surface via the release cord, breaking the partial vacuum between the suction cup and implant surface and releasing the implant from the instrument.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION OF EMBODIMENTS

Figure 1:
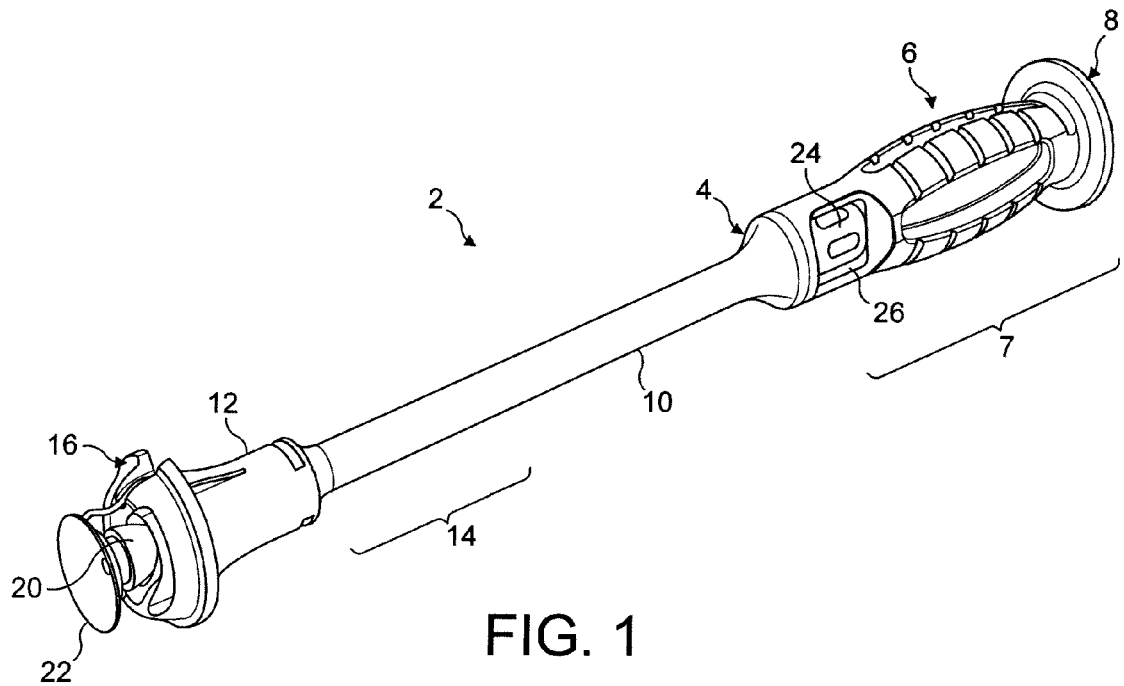
FIG. 1 is a perspective view of an instrument for manipulating an implant.

With reference to FIGS. 1 to 6, an instrument 2 for manipulating an implant comprises a handle 4 having a gripping surface 6 at a proximal end 7 thereof and an impaction surface 8 immediately adjacent the gripping surface 6 and at the extreme proximal end of the instrument 2. The impaction surface 8 extends substantially perpendicular to a longitudinal axis A of the instrument 2 and is operable to receive blows from an impaction device such as a hammer. An elongate main body 10 extends from the gripping surface 6 of the handle along the axis A in a distal direction. An impaction plate 12 is removably mounted on a distal end 14 of the handle. The impaction plate 12 is securely mounted in fixed relation to the handle 4 and comprises an annular impaction surface 16.

The main body 10 of the handle 4 and the impaction plate 12 are substantially hollow, and when assembled together define a longitudinal bore 18 extending therethrough. Received within the bore 18 is an actuation rod 20. An attachment element in the form of a suction cup 22 is mounted on a distal end of the actuation rod 20 and protrudes from a distal end of the instrument 2, adjacent the impaction plate 12. A proximal end of the actuation rod 20 terminates in the region of the gripping surface 6 of the handle 4. An annular drive wheel 24 is mounted within a housing 26 formed in the handle 4 immediately adjacent the gripping surface 6 of the handle 4 on a distal side of the gripping surface 6. The drive wheel 24 is retained within the housing 26 and the proximal end of the actuation rod extends through the drive wheel 24.

Figure 2:
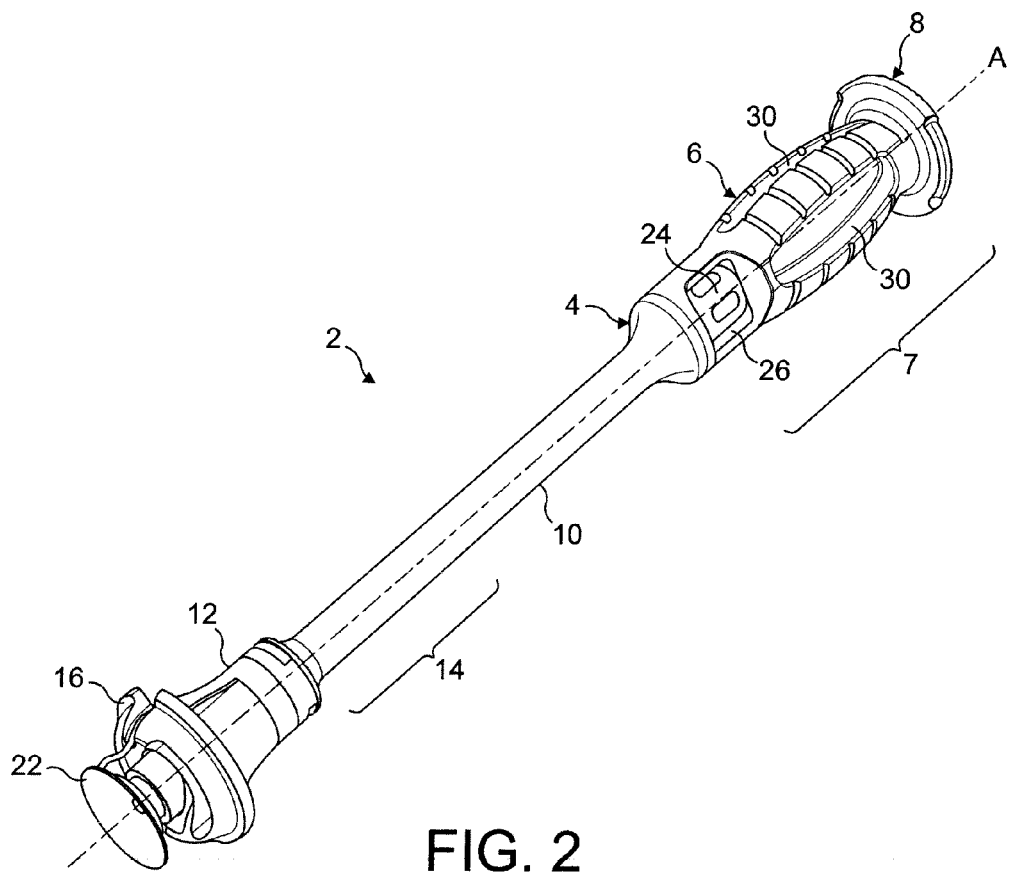
FIG. 2 is another perspective view of the instrument of FIG. 1.
Figure 3:
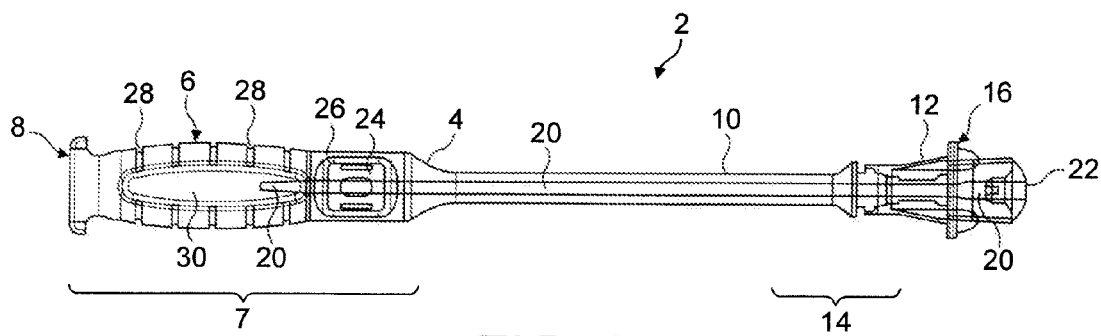
FIG. 3 a side view of the instrument of FIG. 1 showing internal components.
Figure 4:
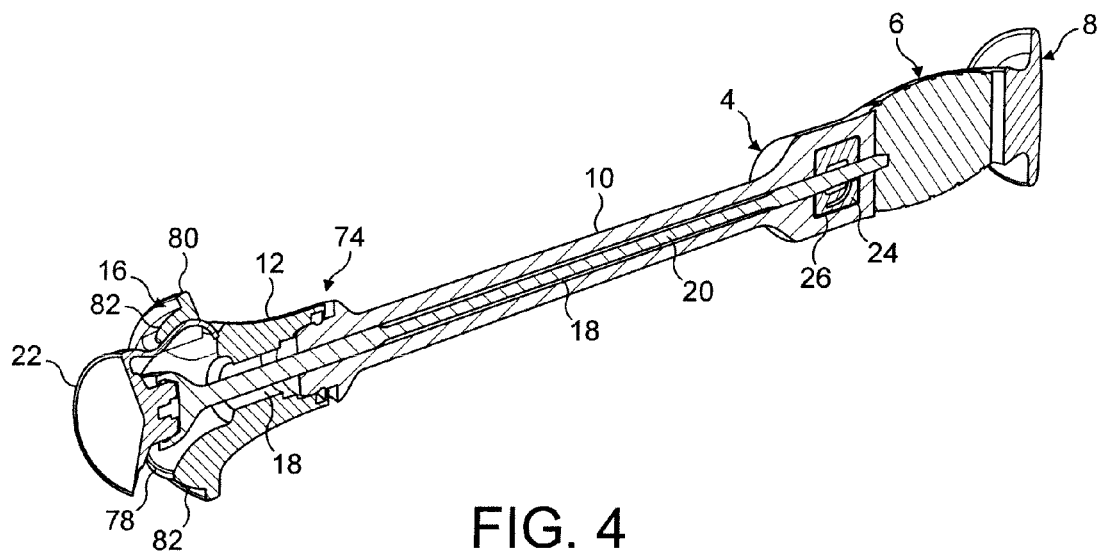
FIG. 4 is a sectional view of the instrument of FIG. 1.
Figure 5:
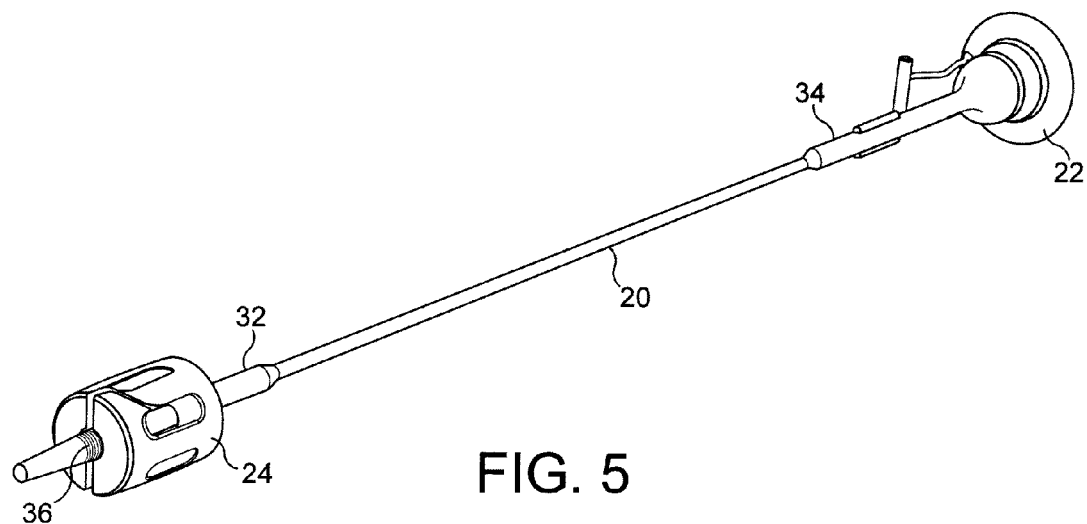
FIG. 5 is a perspective view of an actuation rod with suction cup and drive wheel.
Figure 6:
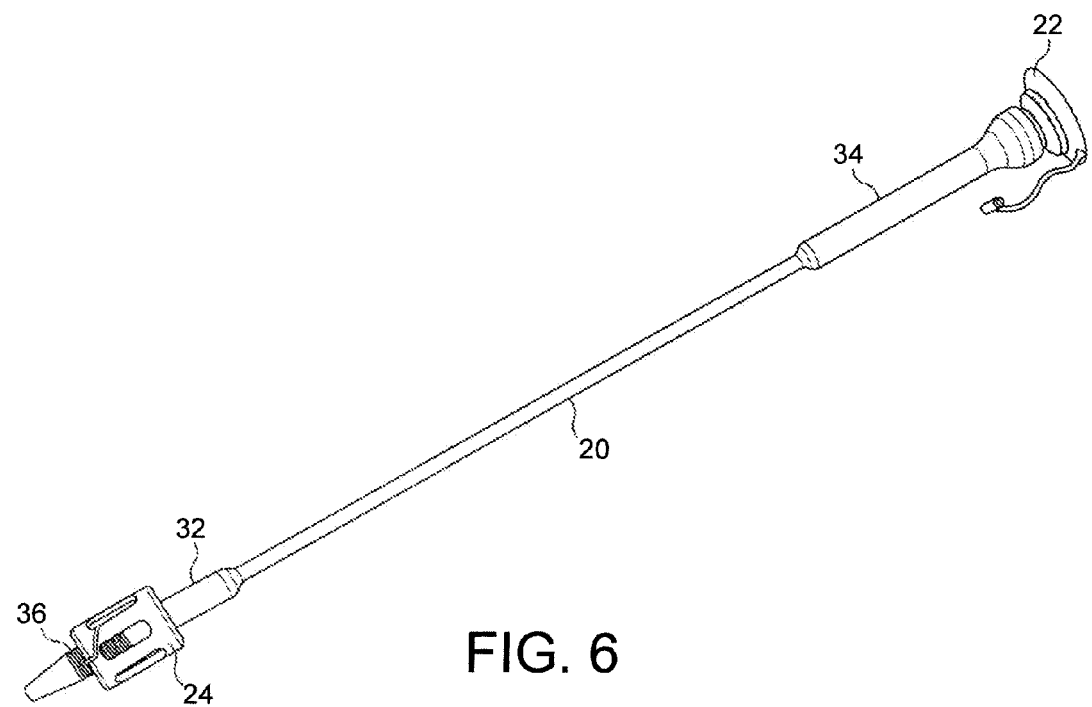
FIG. 6 is another perspective view of the actuation rod of FIG. 5.

With particular reference to FIGS. 2 and 3, the gripping surface 6 of the handle 4 may be formed in any appropriate fashion and may comprise a series of circumferential grooves 28, operable to assist in providing grip for a user. According to one embodiment, the gripping surface 6 is substantially hollow and comprises a plurality of longitudinal recesses 30 extending therethrough. According to another embodiment (not shown) the gripping surface 6 comprises a silicone gripping surface in the form of a substantially cylindrical silicone component moulded or otherwise shaped over the relevant portion of the handle 4. Such a component provides a comfortable non slip surface for the hand of a user.

Referring again to FIGS. 5 and 6, the actuation rod 20 comprises a single cylindrical member which may have increased thickness at its proximal and distal ends 32, 34. The proximal end 32 of the rod 20 carries an external thread 36, further detail of which is provided below. The distal end 34 of the rod 20 widens into an attachment recess, operable to receive an attachment lug of the suction cup 22. Further detail of the attachment between the distal end 34 of the rod 20 and the suction cup 22 is given below.

Figure 7:
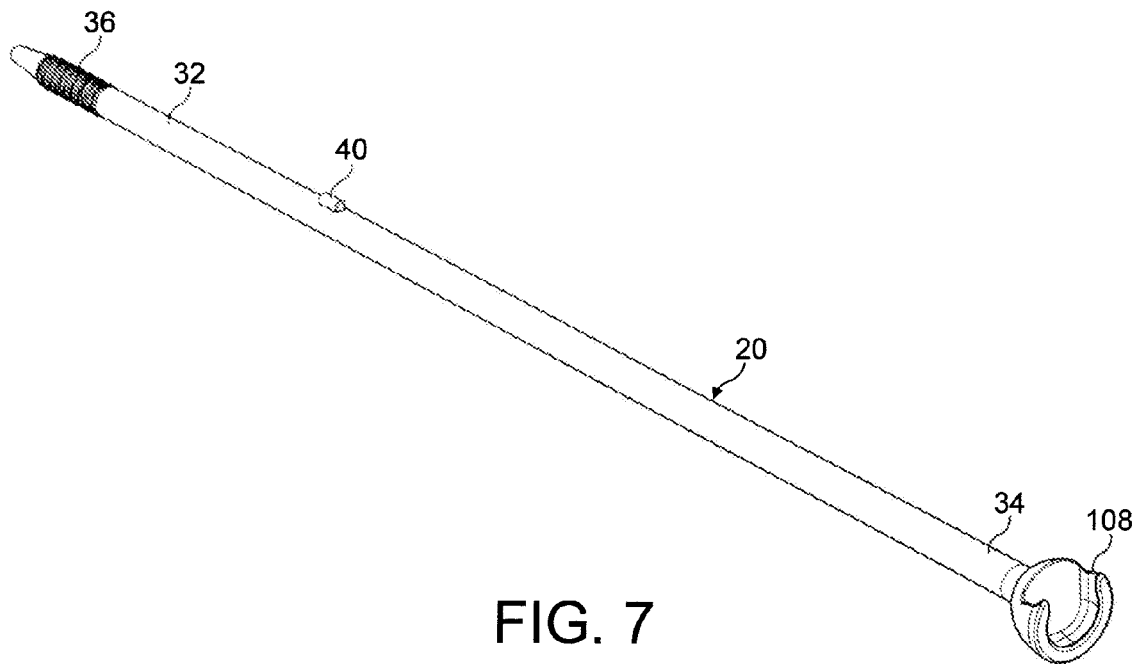
FIG. 7 is a perspective view of an alternative actuation rod.

With reference to FIG. 7, in an alternative embodiment, the actuation rod may be of substantially constant diameter along the extent of the rod and the proximal and distal ends 32, 34.

Figure 8:
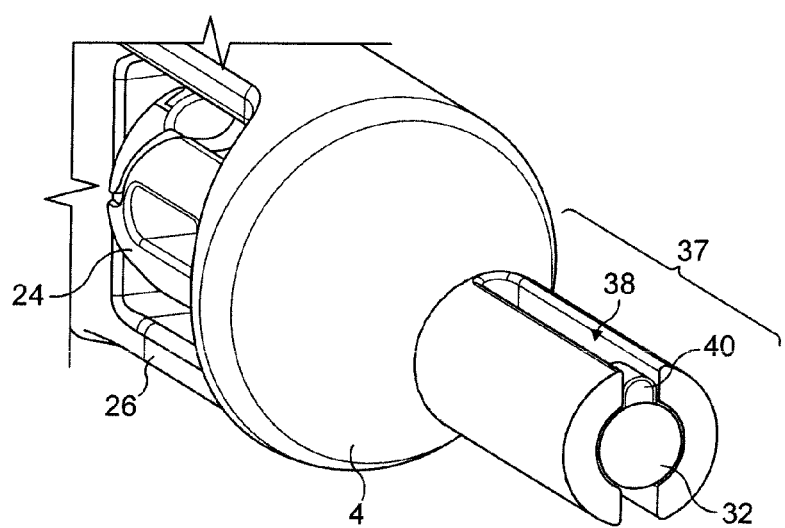
FIG. 8 is an enlarged perspective view of a proximal end of a handle and actuation rod.

The actuation rod 20 extends through the longitudinal bore 18 formed in the handle 4 and impaction plate 12. The actuation rod 20 is slidably received within the bore 18, but is prevented from relative rotation within the bore by an anti rotation feature 37, an embodiment of which is illustrated in FIG. 8. The anti rotation feature 37 illustrated in FIG. 8 comprises a keyway 38 formed in the handle 4 immediately adjacent the housing 26 on the proximal side of the housing 26. Received within the keyway 38 is a spigot 40 formed on the proximal end 32 of the actuation rod 20. The spigot 40 slides longitudinally within the keyway 38 but the close fit between the spigot 40 and the keyway 38 prevents relative rotation between the handle 4 and the actuation rod 20.

In an alternative embodiment, partially illustrated in FIG. 7, the keyway 38 may be formed in the main body 10 of the handle, and the spigot 40 may be formed in an appropriate location along the extent of the actuation rod 20. The appropriate location may be at approximately one third of the length of the rod 20 from the proximal end. The spigot may be considered as an "anti rotation" fin. The keyway 38 may extend along a majority of the length of the handle 4, for example from adjacent the impaction plate 12 to adjacent the housing 26.

Figure 11:
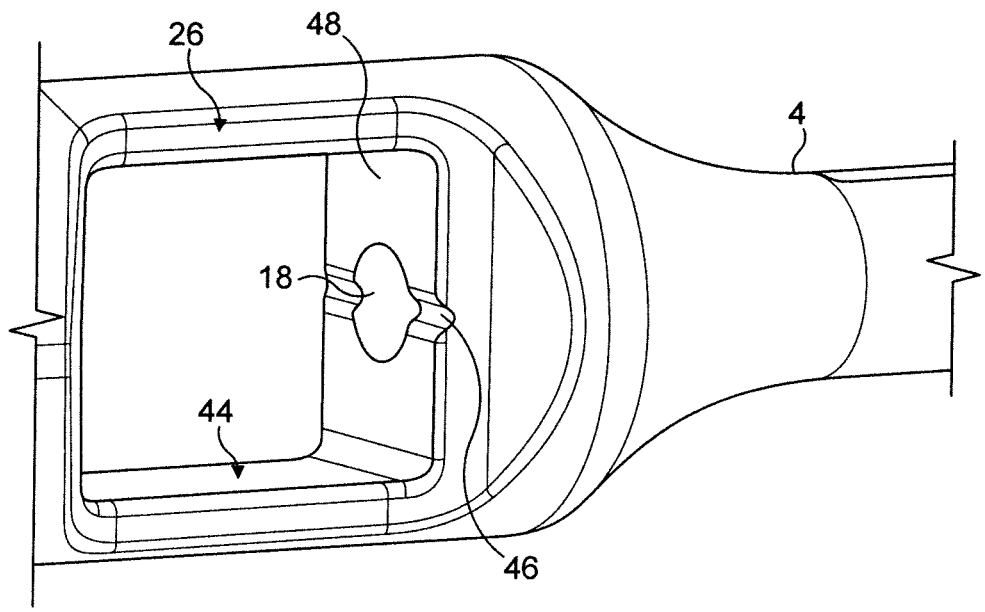
FIG. 11 is a partial perspective view of a handle showing a housing.

With reference to FIGS. 9 to 15, immediately adjacent the gripping surface 6 of the handle 4, on the distal side of the gripping surface 6, is the housing 26, within which is retained the drive wheel 24. The drive wheel 24, engages the actuation rod 20 and housing 26 to form a drive mechanism 42 as explained in more detail below. As shown in FIG. 11, the housing 26 comprises a recess 44 extending through the thickness of the handle 4 immediately adjacent the gripping surface 6. The longitudinal bore 18, which extends through the main body 10 of the handle 4 and the impaction plate 12, opens into the housing 26. A groove 46 extends across the annular distal surface 48 of the housing, either side of the bore 18. Rotatably received within the housing 26 is the drive wheel 24, illustrated in FIGS. 10, 12 and 13. The drive wheel 24 comprises an annular cylindrical wheel having a central bore 50 extending axially therethrough and a plurality of longitudinal recesses 52 opening into the bore 50. The recesses define a plurality of columns 54 which link an annular proximal end of the drive wheel 24 with an annular distal end of the drive wheel 24. The columns 54 form prominent handling portions that facilitate gripping and turning of the drive wheel 24. The bore 50 extending through the drive wheel 24 may be of substantially the same diameter as the bore 18 extending through the handle 4. Alternatively, the bore 50 extending through the drive wheel may be of slightly larger diameter than the bore 18 extending through the handle 4. The two bores 50, 18 communicate with each other and are substantially axially aligned when the drive wheel 24 is in retained within the housing 26.

Figure 12:
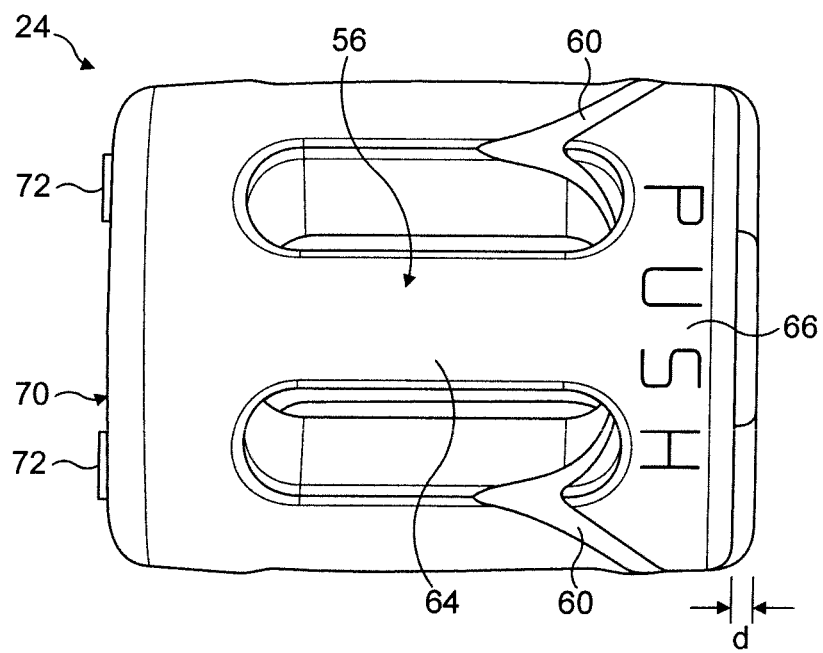
FIG. 12 is a side view of the drive wheel of FIG. 10
Figure 13:
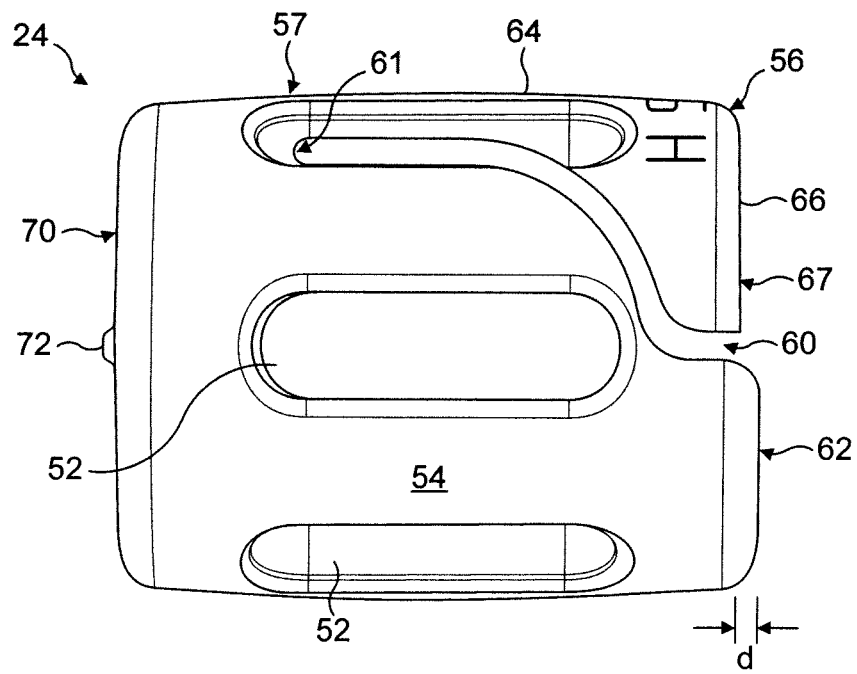
FIG. 13 is another side view of the drive wheel of FIG. 10, rotated approximately 90 degrees with respect to the view of FIG. 12.

The drive wheel 24 comprises a ratchet arm 56, which may be seen most clearly in FIGS. 12 and 13. The ratchet arm 56 is defined by a single curving slot 60, which extends across the drive wheel 24. The slot 60 opens at a proximal end surface of the drive wheel 24, at which point it extends substantially diametrically across the annular proximal surface of the drive wheel 24, across the opening of the bore 50. The slot 60 then curves towards an annular wall of the drive wheel 24, as it extends in a distal direction. The slot 60 extends longitudinally through one of the columns 54, so as to define the ratchet arm 56 radially outwardly of the remainder of the column 54. The base 61 of the slot 60, and the curvature towards the remaining thickness of the adjacent column 54, bisected along its length by the slot 60, can be seen in FIG. 13. The ratchet arm 56 is connected to the remainder of the drive wheel at one end only of the ratchet arm 56. This integral connection is formed at the distal base 57 of the ratchet arm 56, as seen for example in FIG. 13. The curvature of the slot 60 in the longitudinal direction ensures that the ratchet arm 56 widens from a longitudinal portion 64, adjacent the remaining thickness of the corresponding column 54, to an arcuate engaging portion 66. An inner surface of the engaging portion 66 carries an internal thread 68, which may best be seen in FIG. 10. The internal thread 68 is dimensioned to engage with the external thread 36 formed on the proximal end 32 of the actuation rod 20. The remainder of the internal surface of the bore 50 of the drive wheel 24 is substantially smooth, and dimensioned so as not to engage the thread 36 on the actuation rod 20.

The ratchet arm 56 is shorter in the longitudinal direction than the rest of the drive wheel 24. The proximal part annular surface 67 of the engaging portion 66 of the ratchet arm 56 is displaced from the proximal part annular surface 62 of the remainder of the drive wheel 24 by a distance d. This separation acts as a clearance, allowing for ratcheting action of the ratchet arm 56 even when the drive wheel 24 is located immediately adjacent the proximal end wall of the housing 26.

A distal end annular surface 70 of the drive wheel 24 comprises a pair of engagement lugs 72. The lugs 72 protrude from the annular surface 70 on either side of the central bore 50 and are dimensioned to be engageable in the groove 46 extending across the distal annular surface 48 of the housing 26.

Figure 9:
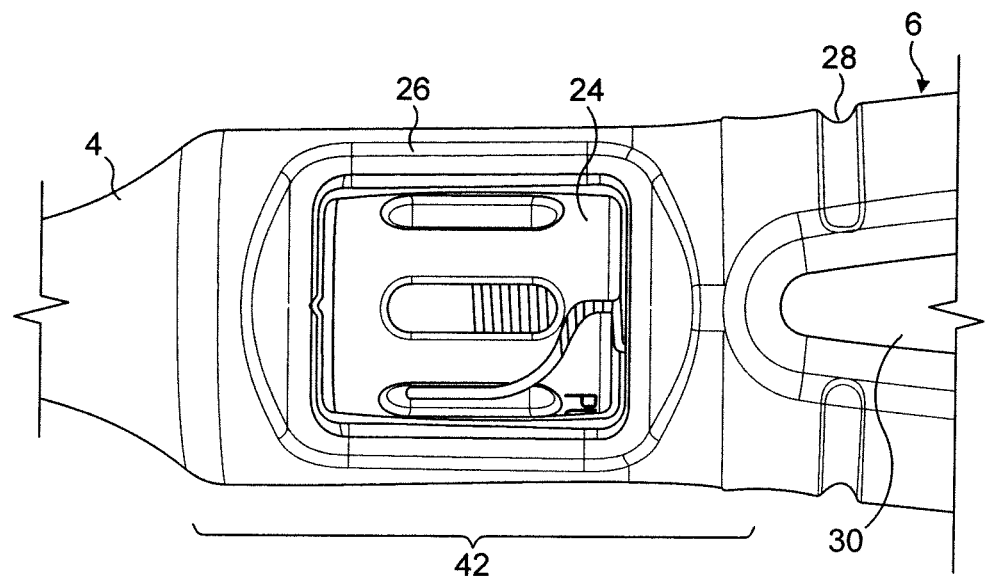
FIG. 9 is a partial side view of a drive mechanism.
Figure 10:
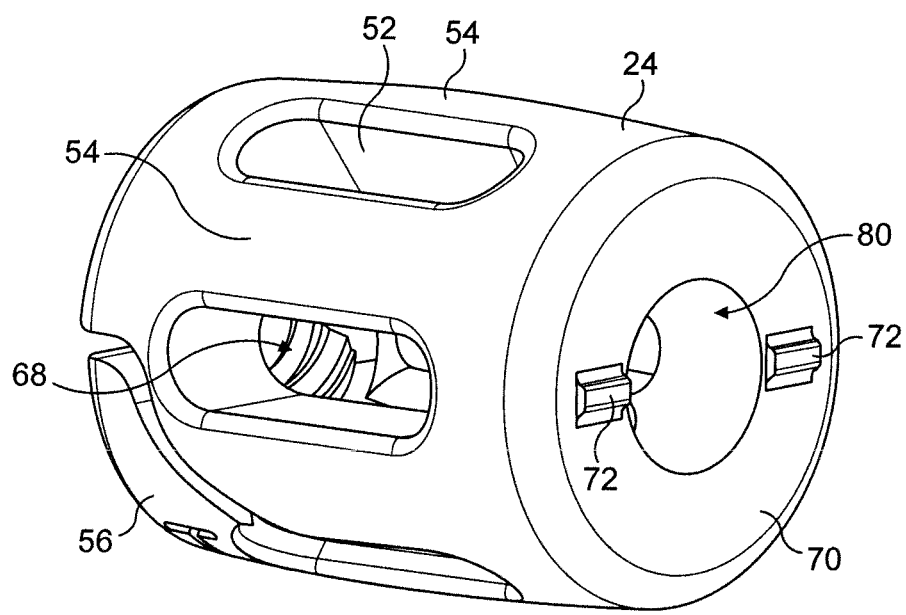
FIG. 10 is a perspective view of a drive wheel.
Figure 14:
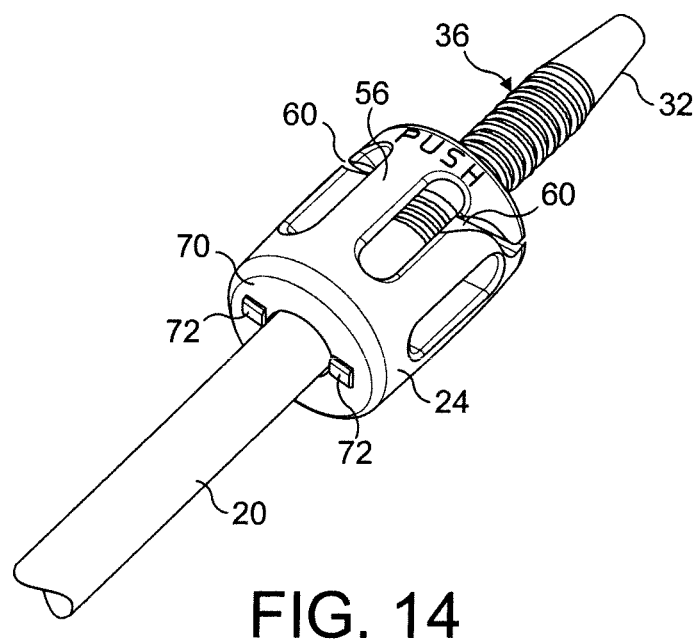
FIG. 14 is a perspective view of an actuation rod and drive wheel.
Figure 15:
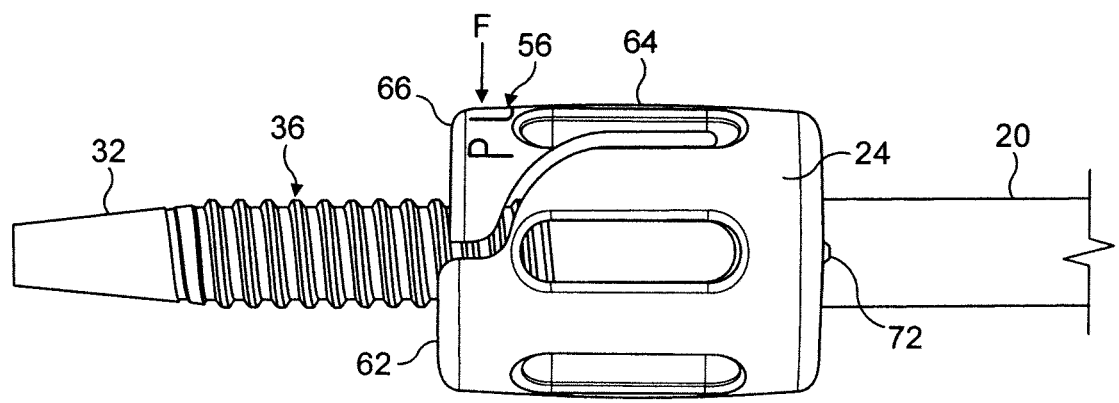
FIG. 15 is a side view of the actuation rod and drive wheel of FIG. 14.
Figure 16:
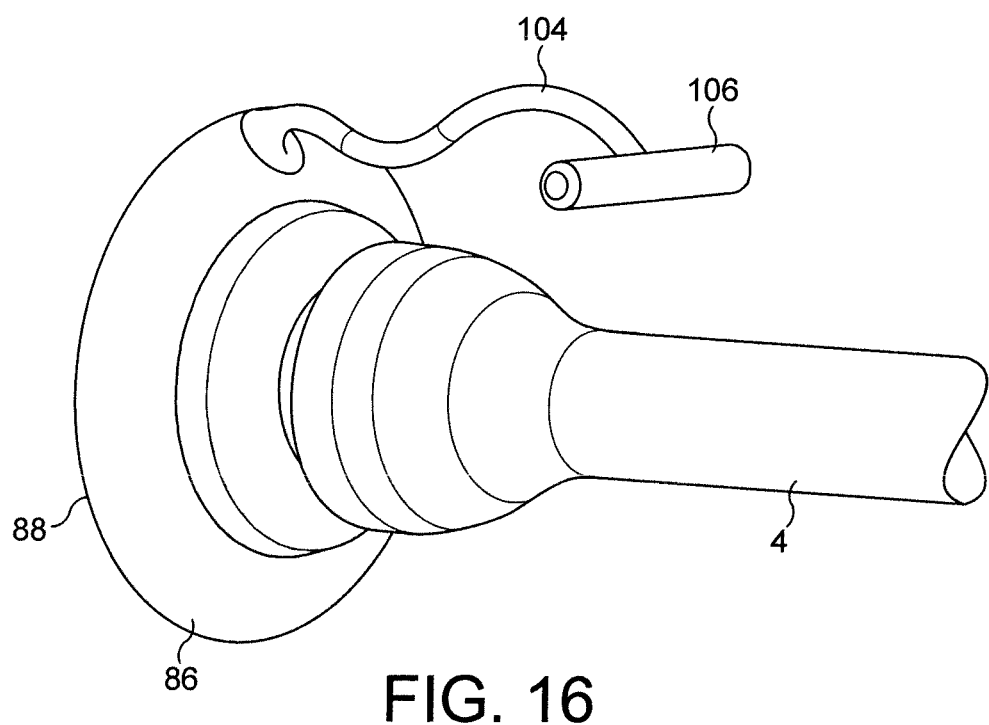
FIG. 16 is a perspective view of a suction cup attached to an actuation rod.
Figure 17:
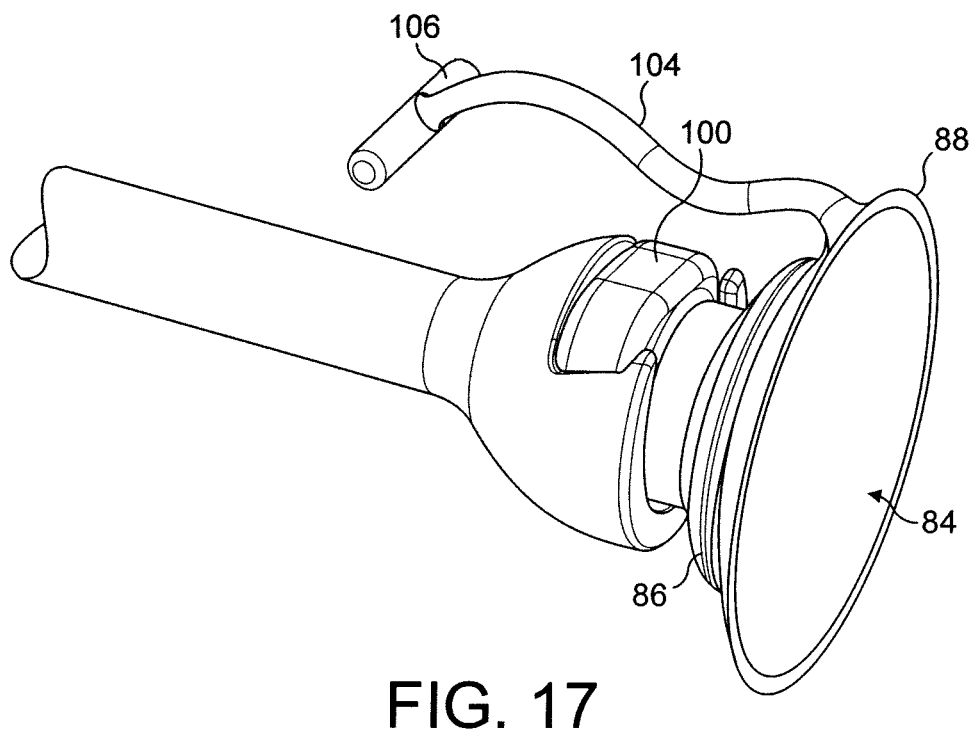
FIG. 17 is a perspective view of a suction cup and attachment rod illustrating the attachment mechanism therebetween.

As seen in FIGS. 9, 14 and 15, the proximal end 32 of the actuation rod 20 is received through the bore 18 in the handle 4 and through the bore 50 in the drive wheel 24. The actuation rod 20 thus helps to retain the drive wheel 24 in place within the housing 26. The housing 26 receives the drive wheel 24 with a degree of play, particularly in the longitudinal direction. Thus, the drive wheel 24 may rotate freely within the housing 26, with the lugs 72 passing over the annular surface 48 of the housing 26. However, if a force is applied to draw the drive wheel 24 towards the distal annular surface 48 of the housing 26, the lugs 72 may be pulled into engagement with the groove 46 thus preventing further rotation of the drive wheel 24 within the housing 26. Such a force is applied when the actuation rod in placed under tension during use of the instrument, as described below.

The ratchet arm 56 of the drive wheel 24 is of a resilient nature, allowing the arm 56 to deform to allow free passage of the actuation rod 20 through the bore in a proximal direction. During passage of the activation rod 20 through the drive wheel 24, each internal thread 68 on the engaging portion 66 of the ratchet arm 56 rides up a corresponding external thread 36 on the actuation rod 20 as the arm 56 deforms, forcing the engaging portion 66 to move away from the actuation rod 20. As the rod 20 passes further in the proximal direction, bringing the internal thread 68 into alignment with the next external thread 36 on the actuation rod 20, the resilient nature of the arm 56 pulls the arm 56 back into position. If an inward radial force is applied to the ratchet arm 56, substantially in direction F in FIG. 15, such ratcheting motion is prevented, and the internal threads 68 on the ratchet arm 56 are forced to remain in engagement with the external threads 36 on the actuation rod 20. In this manner, relative motion between the actuation rod 20 and the drive wheel 24 is constrained. Rotational force applied to the drive wheel 24 causes controlled longitudinal displacement of the actuation rod 20 with respect to the drive wheel 24, and housing 26, as the engaged threads 36, 68 and the anti rotation feature 37 combine to drive and control the motion of the rod 20.

In an alternative embodiment (not shown), the drive wheel as described above may be accommodated substantially at the proximal end of the handle, adjacent to or mounted within an end cap on which the impaction surface 8 is formed. The drive wheel 24 mounted in this location comprises the same features and functions as described above but is simply positioned on the other side of the gripping surface.

Referring again to FIG. 4, the impaction plate 12 of the instrument 2 comprises a solid annular element having a central bore 18 extending there through. The impaction plate 12 is held in position on the distal end 14 of the handle 4 via cooperating connection elements 74 formed on the proximal end of the impaction plate 12 and the distal end of the handle 4. The connection elements 74 may include for example a sprung O ring seal. Alternatively, the connection elements 74 may include cooperating tabs formed on the impaction plate 12 and grooves formed on the handle 4 to receive the tabs in a "snap fit" arrangement. The tabs and grooves (not shown) may cooperate with other anti rotation features such as engaging lugs and recesses, to provide additional stability against relative rotation between the impaction plate 12 and the handle 4. The connection elements 74 hold the impaction plate 12 in fixed relation to the handle 4 but allow for removal of the impaction plate 12 if required, and replacement with an alternative impaction plate 12, having for example a different diameter. The impaction plate bore 18 opens out towards its distal end to be defined at its opening by an annular lip 78. A protruding annular impaction shoulder 80 extends around the impaction plate 12 and defines the distally facing annular impaction surface 16. A curving annular wall 82 extends from the lip 78 of the impaction plate to the annular impaction surface 16. As will be explained in further detail below, the annular impaction surface 16 and curving annular wall 82 are dimensioned so as to correspond to a particular size of acetabular cup implant. The impaction surface 16 is dimensioned to match a rim surface of the implant and the curving wall 82 is dimensioned to be closely received within an internal surface of the implant. The instrument may further comprise a silicone O-ring (not shown) which may be positioned on the curving annular wall 82, substantially adjacent the annular impaction surface 16. The O ring may assist in providing a close sealing relationship between the impaction plate 12 and an implant to be gripped.

The impaction plate 12 may for example be formed from a polymeric material, so as to reduce the weight of the instrument and to reduce the possibility of marking of the implant to be gripped.

Referring now to FIGS. 16 to 20, the suction cup 22 comprises a cup 86 and attachment lug 100, which is connected to a central region of a convex side of the cup 86 by a neck portion 100. The cup 86 defines a concave suction surface 84 that terminates in a circular rim 88. A release cord 104 extends from the rim 88 of the cup and terminates in a T bar shaped release tab 106. The attachment lug 100 is received within a correspondingly shaped recess 108 in the distal end 34 of the actuation rod 20. The extreme distal end of the actuation rod 20 widens to accommodate the recess 108 which is formed as a cut out, with one side open to allow entry of the attachment lug 100 of the suction cup 22. The attachment lug 100 is then held within the recess 108 through a combination of interference fit and the mouth 114 of the recess. The interference fit is provided between the inner wall 110 of the recess and the planar walls 112 of the attachment lug 100, and also between the radially inner surface of the distal wall 111, which defines a distal extent of the recess 108, and the radially outer wall of the neck 102 on the suction cup 22. The mouth 114 of the recess 108 is dimensioned to be smaller than the widest dimension of the attachment lug 100. In this manner, the resilient material of the lug 100 may be deformed to allow entry of the lug 100 into the recess but is then securely held within the recess 108 and may only be removed with the controlled application of force by a user.

Other forms of attachment between the suction cup 22 and the distal end 34 of the actuation rod 20 may be contemplated, providing the suction cup is held securely yet removably in place. For example, push or slide fits involving lugs and corresponding recesses may be employed. The connection between the suction cup 22 and actuation rod 20 must be sufficiently strong to withstand applied axial forces, as explained further below.

The cup 86, neck 102, attachment lug 100, release cord 104 and release tab 106 are integrally formed of medical grade silicone. Other arrangements in which one of more of the component parts of the suction cup 22 are separately formed and connected together may also be contemplated. In addition, other forms of release mechanism may also be envisaged. For example, the release tab and release cord may be formed from a metallic wire, or other suitable material, and the release cord may engage the circular rim 88 of the suction surface 84 via a lug or protrusion formed on the rim 88 for that purpose. The release cord may pass through a small opening on the lug and be secured by a knot or other suitable mechanism.

Figure 18:
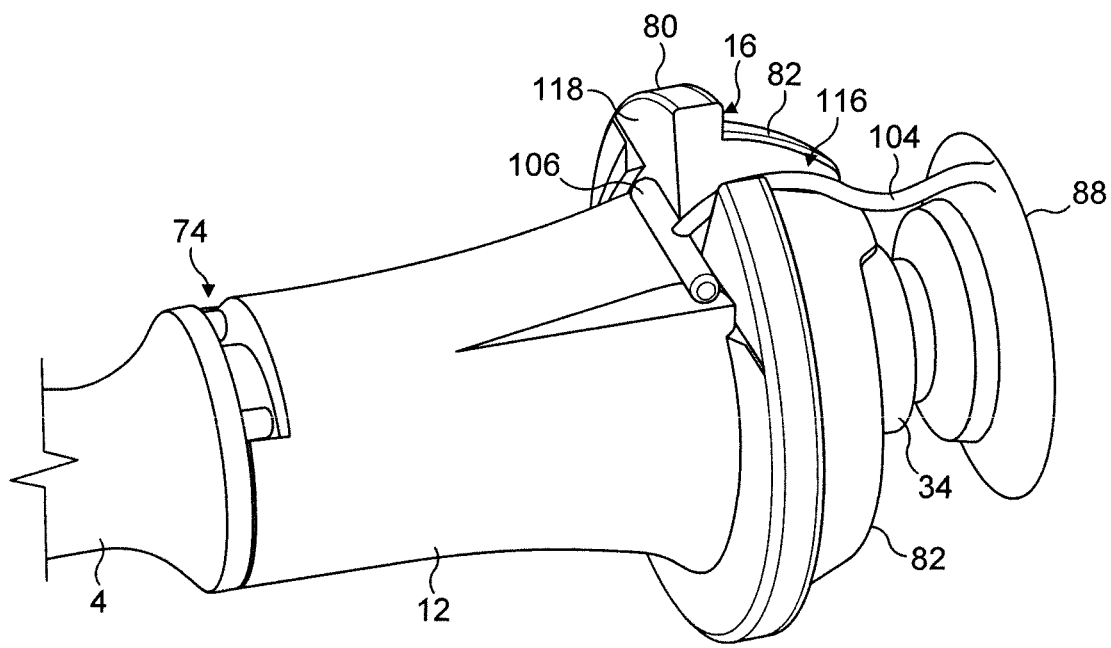
FIG. 18 is a perspective view of a distal end of the instrument of FIG. 1.
Figure 19:
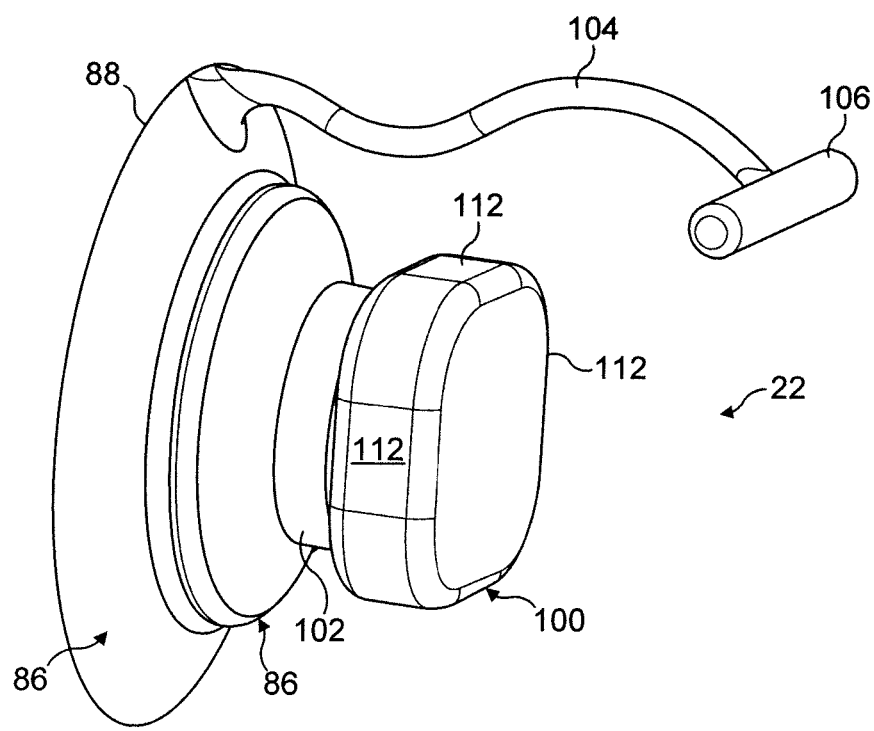
FIG. 19 is a perspective view of a suction cup.
Figure 20:
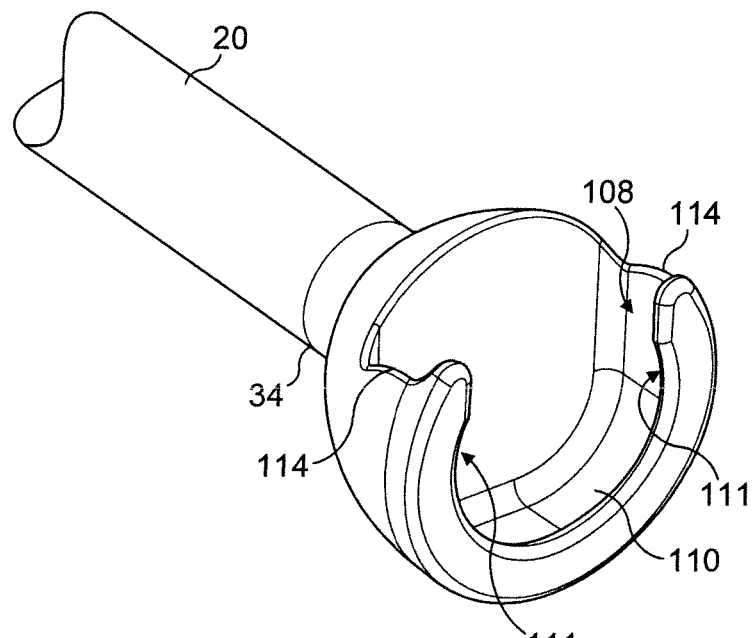
FIG. 20 is a perspective view of a distal end of an actuation rod.
Figure 21:
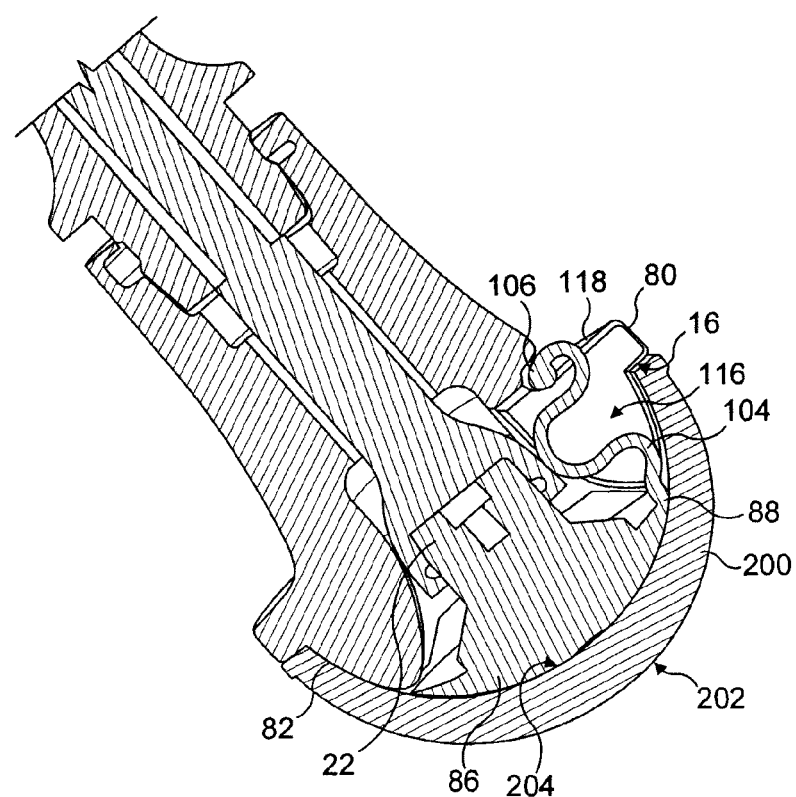
FIG. 21 is a sectional view of a distal end of the instrument of FIG. 1 engaged on an implant.
Figure 22:
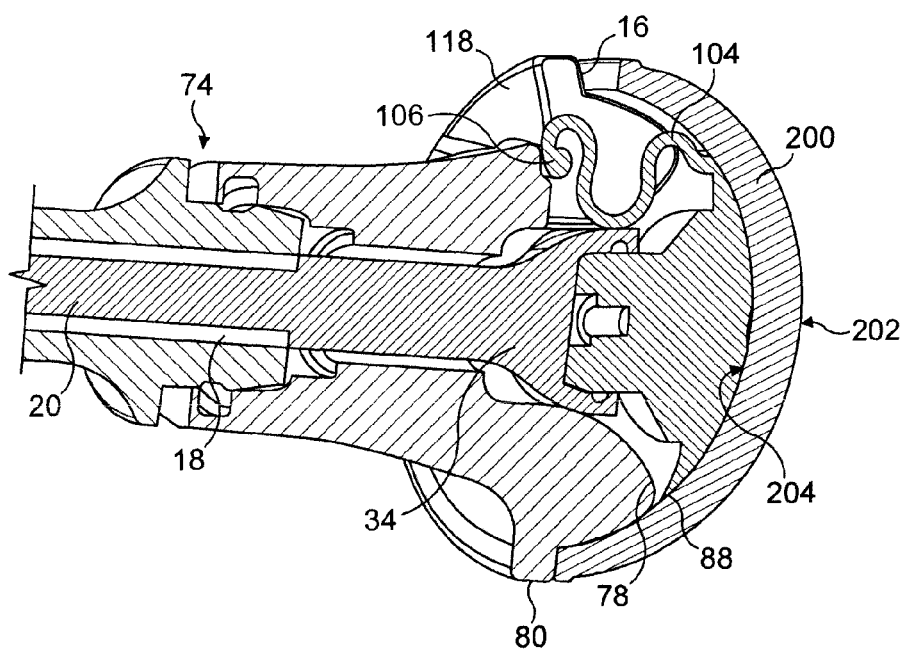
FIG. 22 is another sectional view of the instrument of FIG. 21.

With the suction cup 22 attached to the actuation rod 20, and with the actuation rod 20 received within the handle 4 and impaction plate 12, the release cord 104 passes through a radial recess or slot 116 in the impaction plate 12 and the release tab 106 engages on a release surface 118 formed on the opposite side of the annular impaction shoulder 80 to the annular impaction surface 16. This arrangement is illustrated in FIG. 18. If an O ring is present, the o ring may extend over the release cord 104.

Use of the instrument 2 to grip, manoeuvre and impact a Monoblock acetabular cup prosthesis is described below with reference to FIGS. 21 to 24. It will be appreciated that the instrument 2 may be used prior to any surgical procedure, simply to move the prosthesis in a convenient manner, or may be used during a joint replacement procedure to position and impact the prosthesis. An acetabular cup prosthesis 200 for which the instrument 2 is particularly suited comprises a substantially hemispherical one piece prosthesis comprising an external bone engaging surface 202 and a concave internal bearing surface 204. Before applying the instrument 2 to the acetabular cup prosthesis 200, a user first grasps the handle 4 of the instrument 2 at the gripping surface 6, and applies pressure to the ratchet arm 56 of the drive wheel 24, substantially in the region marked "PUSH" in FIG. 12. This pressure holds the cooperating threads 68, 36 of the ratchet arm 56 and actuation rod 20 in engagement, thus preventing ratcheting action of the arm 56. The pressure also prevents rotation of the drive wheel 24 relative to the handle 4 and so inhibits any relative sliding motion of the actuation rod 20 within the handle 4.

With pressure applied as described above, the distal end of the instrument 2 is brought into contact with the concave bearing surface 204 of the prosthesis 200, substantially at the pole of the prosthesis. The cup 86 of the suction cup 22 deforms to bring the suction surface 84 of the cup 86 into contact with the bearing surface 204 and form at least a partial vacuum therebetween. Once a vacuum has been established and the cup 86 is fully engaged on the bearing surface 204 of the prosthesis 200, the user releases pressure on the ratchet arm 56 of the drive wheel 24 and applies force to the handle 4, causing the handle 4 to approach the prosthesis 200. With the prosthesis firmly engaged on the suction cup 22 at the end of the actuation rod, such pressure causes relative movement of the handle along the actuation rod towards the prosthesis and the distal end 34 of the actuation rod 20. Such relative motion is allowed by the ratcheting action of the ratchet arm 56, which deforms to allow free passage of the drive wheel 24, and hence the handle 4, over the threads 36 of the actuation rod 20. During this motion, the drive wheel 24 is engaged against the proximal face of the housing 26, and the pivoting motion of the ratchet arm 56 is thus facilitated by the clearance d between the proximal end surface 67 of the ratchet arm 56, and the proximal end surface 62 of the remainder of the drive wheel 24. The handle 4 slides along the actuation rod 20 substantially in a single movement until the annular impaction surface 16 of the impaction plate 12 engages on the annular rim of the prosthesis 200. The curved annular wall 82 immediately distal of the annular impaction surface 16 is closely received within the upper reaches of the bearing surface 204 of the prosthesis 200. The curving annular wall 82, in cooperation with the silicone O ring, if present, helps to centre the instrument 2 on the prosthesis 200 and to maintain this centring throughout use of the instrument 2.

With the annular impaction surface 16 fully engaged on the rim of the prosthesis, the user ensures that the cooperating threads 68, 36 of the ratchet arm 56 and actuation rod 20 are fully engaged, and then imparts a turning force on the drive wheel 24, causing the actuation rod 20 to be drawn further into the handle 4. This action forces the annular impaction surface 16 against the rim of the acetabular cup 200 and acts to draw the distal end of the actuation rod, and hence the centre of the suction cup 22, away from the bearing surface 204 of the prosthesis 200, retracting the actuation rod 20 into the handle 4. This action increases the partial vacuum between the suction surface 84 of the cup 86 and the bearing surface 204, further reinforcing the engagement between the instrument 2 and the prosthesis 200, in effect tightening the fit of the instrument 2 on the prosthesis 200. This drawing action causes minor deformation of the resilient material of the suction cup 22, resulting in a tensile force carried by the actuation rod. This tensile force acts to pull the rod 20 out of the handle 4 back towards the prosthesis 200, so as to relieve the vacuum under the suction surface 86. The force also therefore acts to pull the distal annular surface of the drive wheel 24 against the distal annular surface 48 of the housing 26. In order to prevent further relative rotation of the drive wheel 24, and hence sliding of the actuation rod 20 out of the handle 4, the user rotates the drive wheel 24 until the lugs 72 on the drive wheel 24 engage into the groove 46 on the housing surface 48. The tensile force carried through the actuation rod 20 pulls the lugs 72 into engagement with the groove 46, and the deformable nature of the suction cup 22 allows for rotation of the drive wheel, and attendant translation of the actuation rod, until the lugs 72 align with the groove 46. With the lugs 72 engaged in the groove 46, the instrument 2 is effectively locked in position with the prosthesis 200 securely held at the distal end. The prosthesis 200 may then be moved, positioned or otherwise manipulated as required. If being impacted, the prosthesis 200 may be placed in the required location and orientation, and impaction force may then be imparted via the main impaction surface 8. The engagement of the lugs 72 in the groove 46 prevents the thumb wheel effectively "unscrewing" under the impaction forces.

An alignment guide may be used in conjunction with the instrument 2 to ensure that the prosthesis 200 is implanted into a patient acetabulum in the correct orientation. The alignment guide may take any appropriate form to provide angular orientation to the instrument with respect to local and global patent anatomy. In one embodiment, the alignment guide may be a separate component that engages onto the handle 4 in a "snap fit" arrangement. The alignment guide may include openings for additional indicating components and may for example be operable to indicate a horizontal or vertical reference axis or other reference features.

Figure 23:
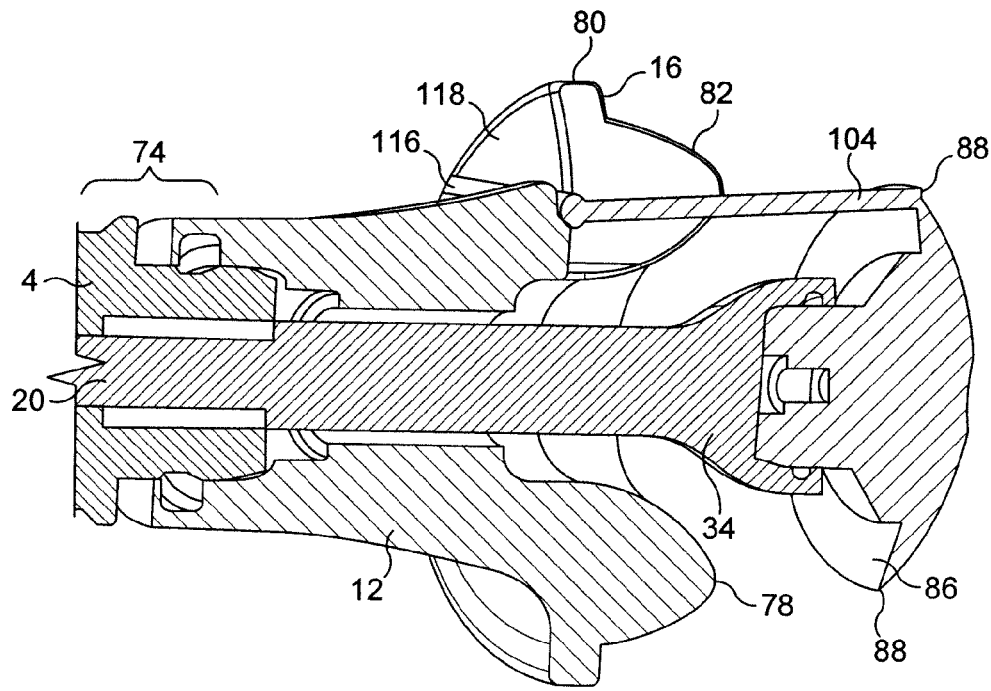
FIG. 23 is a sectional view of the instrument of FIG. 21 on release from the implant.
Figure 24:
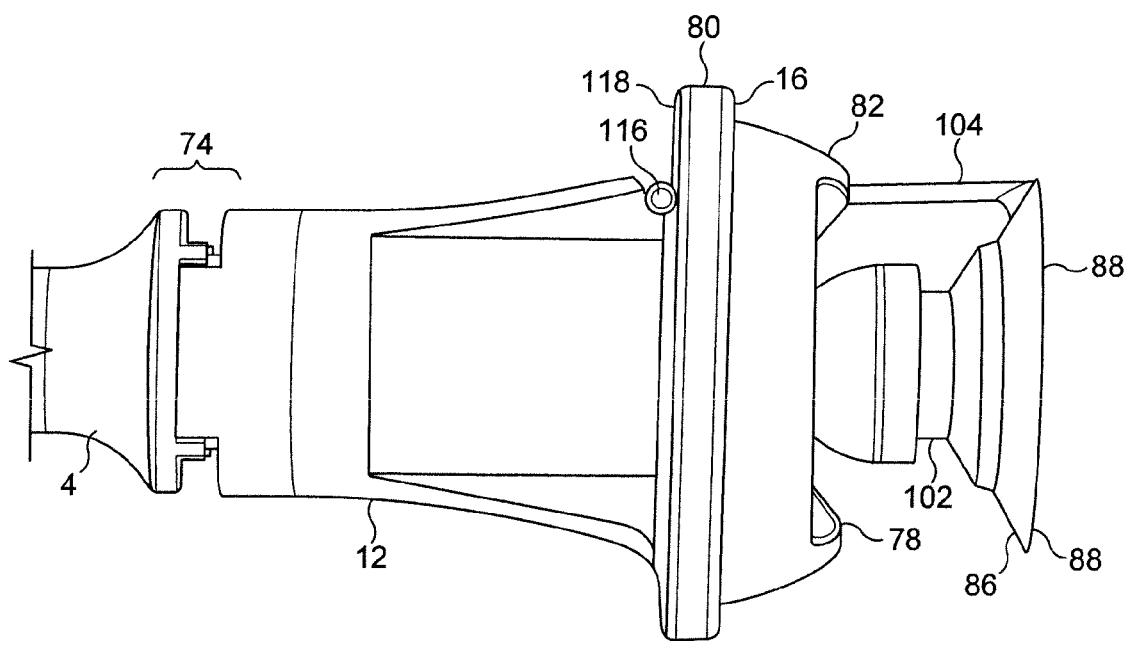
FIG. 24 is a side view of the instrument of FIG. 21 on release from the implant.

Once manipulation of the prosthesis 200 is complete, the user releases the prosthesis 200 from the instrument. This is achieved by turning the drive wheel 24 in the opposite direction to that required for tightening the engagement of the suction cup 22. This rotation of the drive wheel 24 first relaxes the additional vacuum forces applied to the cup and causes the actuation rod 20 to translate gradually out of the distal end of the handle. This movement separates the annular impaction surface 16 from the rim of the prosthesis and gradually separates the impaction plate 12 and handle 4 from the prosthesis 200. During this separation, the release cord 104, which was tightly curled within the radial slot 116 during engagement with the prosthesis 200, gradually unfurls, until it is fully extended between the rim 88 of the cup 86 and the release surface 118 of the impaction plate 12. Further translation of the actuation rod 20 and suction cup 22 away from the impaction plate 12 cannot be accommodated by the release cord 104, and with the release tab 106 fully engaged on the release surface 118 of the impaction plate 12, the release cord 104 starts to peel back the rim 88 of the suction cup 22 away from the bearing surface 204 of the prosthesis 200. Eventually, the displacement between suction cup 22 and impaction plate 12 causes peel back of the rim 88 to an extent that the vacuum seal between the suction surface 86 and the bearing surface 204 is broken, and the prosthesis 200 is released from the instrument 2, as best shown in FIG. 23.

Although operation of the instrument for gripping and impaction of a monoblock acetabular cup has been described, it will be understood that substantially the same steps are followed for gripping and manipulation of an acetabular bearing component for insertion into an acetabular shell.

The instrument 2 of the present invention thus allows for both fast and easy engagement and release of a prosthesis component. It will be appreciated that both activation of suction and release of the prosthesis may be effected from the vicinity of the gripping surface 6 of the handle. At no time is a user required to handle the instrument at or near the prosthesis itself. Operation of the instrument is conducted entirely outside of any patient incision, and one handed operation of the instrument is easily achievable. Such remote operation is not only safer and more ergonomic but is advantageous in preventing contamination of the prosthesis and in minimising handling of the prosthesis when in position. The suction engagement of the prosthesis ensures that the prosthesis itself may be of simple construction, without any designated attachment features. The suction cup also causes no damage to the bearing surface, ensuring that the implant is in perfect condition following implantation.

The impaction plate 12 of the instrument is, as noted above, removable. This allows for a range of impaction plates to be supplied, tailored to particular implant types and sizes. The impaction plates are held securely once connected to the handle 4 of the instrument 2, but are completely interchangeable according to the requirements of the user.

It will also be appreciated that the instrument of the present invention is suitable for use with a range of prostheses, and not just with an acetabular prosthesis as has been described. For example, the instrument may be used in connection with shoulder prostheses and various other implant components.

Figure 25:
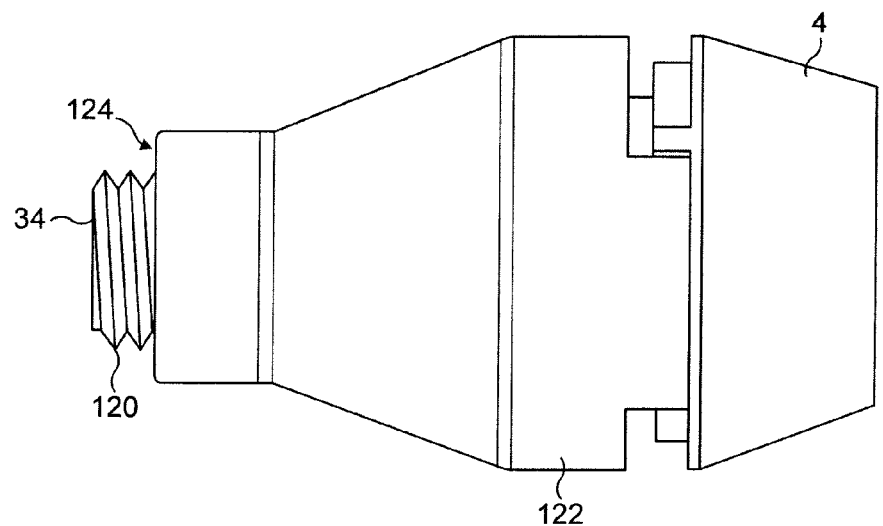
FIG. 25 is a side view of a distal end of another embodiment of instrument.

In an alternative embodiment of the present invention, illustrated in FIG. 25, the suction cup 22 of the instrument 2 may be replaced by an external thread 120 formed on the distal end 34 of the actuation rod 20. The distal end 34 of the actuation rod 20 and its external thread 120 may be dimensioned so as to engage with an apical threaded bore formed on an acetabular shell. A corresponding impaction plate 122 replaces the impaction plate 12 described above with respect to the first embodiment. The alternate impaction plate 122 is designed and dimensioned to cooperate with an acetabular shell component having an apical bore, and the impaction plate 122 thus comprises a much smaller annular impaction surface to engage on the surface of the shell surrounding the apical bore. It will be appreciated that such a shell will be covered by a separate bearing component when in use, so impaction forces may be transmitted directly to the concave inner surface of the shell without fear of damaging the vital bearing surface. In use, the instrument is screwed into and out of engagement with the shell as required by turning the handle. Once fully engaged in the bore, the drive mechanism 42 may be used to tighten the engagement, withdrawing the actuation rod 22 to increase friction on the engaged threads of the actuation rod and the apical bore of the shell.

Figure 26:
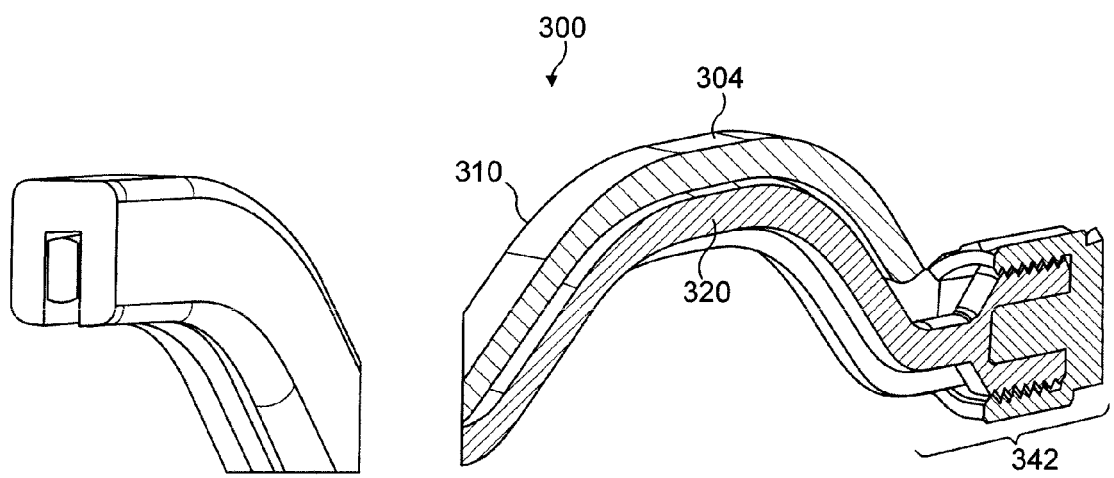
FIG. 26 is a part sectional view of another embodiment of instrument.

In another alternative embodiment, illustrated in FIG. 26, the principles of the instrument 2 may be embodied in an instrument 300 having a curved handle 304. The instrument 300 comprises essentially the same elements as the instrument 2 described above, including a handle gripping surface (not shown), handle main body 310, drive mechanism 342, impaction plate (not shown) and suction cup (not shown). However, the linear actuation rod 20 is replaced with a flexible actuation wire, running through a curved cannulised tube. The wire is translated within the tube and handle by the action of the drive mechanism in the manner described above with respect to the first embodiment of instrument 2. The flexible nature of the actuation wire accommodates the curve in the handle main body. Alternatively, the handle main body may have a U shaped cross section, as illustrated in FIG. 26. This U shaped cross section may have a solid internal bar 320 running inside it. The bar is operable to slide within the U shape section of the handle 304.

The invention claimed is:

1. An instrument for manipulating an implant, the instrument comprising;
   an attachment element comprising a suction cup operable to engage an implant;
   an actuation rod, a distal end of which is connected to the attachment element;
   a handle having a gripping surface, wherein at least a proximal end of the actuation rod is movably received within the handle; and
   a drive mechanism mounted on the handle and comprising an annular wheel, through which the proximal end of the actuation rod is received, the annular wheel comprising an internal thread, structured to engage a corresponding external thread formed on the proximal end of the actuation rod;
   wherein rotation of the annular wheel in a first direction moves the actuation rod relative to the handle to draw the suction cup toward the handle.

2. The instrument as claimed in claim 1, wherein the drive mechanism is mounted in the vicinity of the gripping surface.

3. The instrument as claimed in claim 1, wherein the actuation rod and the handle comprise cooperating formations operable to prevent relative rotation between the actuation rod and the handle.

4. The instrument as claimed in claim 1, wherein the annular wheel comprises a resilient ratchet arm on which the internal thread is formed, a remaining internal surface of the annular wheel being substantially free of surface features.

5. The instrument as claimed in claim 1, wherein the annular wheel is received within a recess formed on the handle.

6. The instrument as claimed in claim 1, wherein adjacent annular surfaces of the wheel and handle comprise cooperating formations operable to engage to limit relative rotation between the wheel and the handle.

7. The instrument as claimed in claim 1, further comprising an impaction plate removably mounted at a distal end of the handle.

8. The instrument as claimed in claim 7, wherein the impaction plate is mounted in fixed relation to the handle.

9. The instrument as claimed in claim 8, wherein the impaction plate comprises an annular impaction surface, operable to engage an annular surface of the implant.

10. The instrument as claimed in claim 1, wherein the suction cup comprises:
    a release mechanism including a release tab, operable to be held in fixed relation to the handle and connected to an edge of the suction cup via a release cord;
    wherein rotation of the annular wheel in a second direction moves the actuation rod relative to the handle extending the suction cup toward the handle to tension the release cord to flex the release tab and deform the suction cup, wherein the second direction is opposite the first direction.

11. The instrument as claimed in claim 10, wherein the release tab is operable to engage a corresponding release surface formed on an impaction plate mounted at a distal end of the handle.

12. The instrument as claimed in claim 10, wherein the release cord is integrally formed with the suction cup.

13. The instrument as claimed in claim 1, wherein the instrument is for gripping and impaction of an implant.

14. An instrument for manipulating an implant, the instrument comprising:
    a handle;
    a suction cup operable to engage a surface of an implant movably mounted with respect to the handle;
    a release cord, fixedly connected between an edge of the suction cup and the handle; and
    an actuation rod movably mounted within the handle, wherein the suction cup is connected to an end of the actuation rod,
    wherein the actuation rod is moveable to draw the suction cup toward the handle to create a suction to engage the surface of the implant, wherein the actuation rod is moveable to push the suction cup away from the handle to tension the release cord to deform the suction cup and release the suction cup from the surface of the implant.

15. The instrument as claimed in claim 14, wherein the release cord is integrally formed with the suction cup and terminates in a release tab.

16. The instrument as claimed in claim 15, further comprising an impaction plate mounted in fixed relation to the handle.

17. The instrument as claimed in claim 16, wherein the release tab is operable to engage a release surface formed on the impaction plate.

* * * * *

UNITED STATES PATENT AND TRADEMARK OFFICE
CERTIFICATE OF CORRECTION

PATENT NO. : 9,782,154 B2
APPLICATION NO. : 13/991040
DATED : October 10, 2017
INVENTOR(S) : Slade et al.

Page 1 of 1

It is certified that error appears in the above-identified patent and that said Letters Patent is hereby corrected as shown below:

In the Claims

In Column 13, Line 36, in Claim 1, delete "comprising;" and insert --comprising:-- therefor Signed and Sealed this
Twenty-eighth Day of May, 2019

Andrei Iancu
*Director of the United States Patent and Trademark Office*